United States Patent
Sun et al.

(10) Patent No.: US 9,089,583 B2
(45) Date of Patent: Jul. 28, 2015

(54) PHARMACEUTICAL COMPOSITION FOR STRENGTHENING SPLEEN AND STOMACH AND PREPARATION METHOD THEREFOR

(75) Inventors: Dejun Sun, Jilin (CN); Jinlong Yin, Jilin (CN); Miaonan Sun, Jilin (CN); Yizhuo Zhao, Jilin (CN); Chunsheng Guo, Jilin (CN); Yanhui Gao, Jilin (CN); Xue Li, Jilin (CN)

(73) Assignee: Jilin Zixin Pharmaceutical Research Institution LLC., Changchun, Jilin (CN)

( * ) Notice: Subject to any disclaimer, the term of this patent is extended or adjusted under 35 U.S.C. 154(b) by 0 days.

(21) Appl. No.: 13/980,878

(22) PCT Filed: Jul. 15, 2011

(86) PCT No.: PCT/CN2011/077176
§ 371 (c)(1),
(2), (4) Date: Jul. 20, 2013

(87) PCT Pub. No.: WO2012/097578
PCT Pub. Date: Jul. 26, 2012

(65) Prior Publication Data
US 2013/0295079 A1 Nov. 7, 2013

(30) Foreign Application Priority Data
Jan. 21, 2011 (CN) .......................... 2011 1 0023836

(51) Int. Cl.
| | | |
|---|---|---|
| *A61K 35/00* | (2006.01) | |
| *A61K 35/66* | (2015.01) | |
| *A61K 36/076* | (2006.01) | |
| *A61K 36/258* | (2006.01) | |
| *A61K 36/284* | (2006.01) | |
| *A61K 36/484* | (2006.01) | |
| *A61K 36/62* | (2006.01) | |
| *A61K 36/734* | (2006.01) | |
| *A61K 36/752* | (2006.01) | |
| *A61K 36/884* | (2006.01) | |
| *A61K 36/8945* | (2006.01) | |
| *A61K 36/8998* | (2006.01) | |
| *A61K 35/745* | (2015.01) | |
| *A61K 35/747* | (2015.01) | |

(52) U.S. Cl.
CPC .............. *A61K 35/66* (2013.01); *A61K 35/745* (2013.01); *A61K 35/747* (2013.01); *A61K 36/076* (2013.01); *A61K 36/258* (2013.01); *A61K 36/284* (2013.01); *A61K 36/484* (2013.01); *A61K 36/62* (2013.01); *A61K 36/734* (2013.01); *A61K 36/752* (2013.01); *A61K 36/884* (2013.01); *A61K 36/8945* (2013.01); *A61K 36/8998* (2013.01)

(58) Field of Classification Search
None
See application file for complete search history.

(56) References Cited

FOREIGN PATENT DOCUMENTS

| | | |
|---|---|---|
| CN | 101091778 A | * 12/2007 |
| EP | 1169925 A1 | * 1/2002 |

OTHER PUBLICATIONS

Yan, Shi Lin and Li, Zheng-Hau, Pathomechanisms of the Spleen, translated by Sabine Wilms, edited by Nigel Wiseman, Paradigm Publications, Taos, New Mexico, 2009.*
Yoon et al. "Fermentation of beet juice by beneficial lactic acid bacteria", Lebensmittel-Wissenschaft & Technologie 38: 73-75, 2005.*
Frauenfelder "Making sauerkraut is easy", Boing Boing website, available online 2009.*
Kotzamanidis et al. "Optimization of lactic acid production from beet molasses by *Lactobacillus delbrueckii* NCIMB 8130", World Journal of Microbiology & Biotechnology 18: 441-8, 2002.*
Xu, CN 101091778 A, GPSN translation.*
Effect of bifidobacterium fermented mixed fruit and vegetable juice on immunological function of mice.

* cited by examiner

*Primary Examiner* — Ruth Davis
*Assistant Examiner* — Emily Cordas

(57) ABSTRACT

A pharmaceutical composition for strengthening spleen and stomach and a preparation method therefor. The method includes the step of mixing four substances listed below to obtain a mixture, wherein the mixture is the pharmaceutical composition for strengthening spleen and stomach, and the four substances are (A) ginseng ethanol extract, (B) volatile oil of largehead atractylodes rhizome and tangerine peels, (C) aqueous extract of Indian bread, yamaimo, lotus seeds, tangerine peels, liquorice root, hawthorn fruit, germinated barley, largehead atractylodes rhizome and rhizoma alismatis; (D) fermentation broth of fruits and vegetables.

2 Claims, No Drawings

PHARMACEUTICAL COMPOSITION FOR STRENGTHENING SPLEEN AND STOMACH AND PREPARATION METHOD THEREFOR

CROSS REFERENCE OF RELATED APPLICATION

This is a U.S. National Stage under 35 U.S.C. 371 of the International Application PCT/CN2011/077176, filed Jul. 15, 2011, which claims priority under 35 U.S.C. 119(a-d) to CN 20110023836.X, filed Jan. 21, 2011.

BACKGROUND OF THE PRESENT INVENTION

1. Field of Invention

The present invention relates to a pharmaceutical composition for strengthening spleen and stomach and a preparation method therefor.

2. Description of Related Arts

Dyspepsia is a clinical syndrome, which is a disease caused by gastric dynamic dysfunction. Dyspepsia also includes gastroparesis and gastroesophageal reflux disease caused by bad peristole. Dyspepsia could be mainly divided into functional dyspepsia and organic dyspepsia. The symptoms are discomfort or pain in the upper abdominal intermittent, fullness, heartburn (reflux), belching, etc. The patient usually does not want to take food or takes food as few as possible because of discomforts such as sense of suppression in the chest, early full feeling, and abdominal distension. The patient could not fall asleep easily at night, and usually has nightmares after falling asleep. In the medical inspection of the hospital, except that mild gastritis could be detected under the gastroscope, other abnormal performances could not be detected through other inspections, such as B ultrasound, radiography, and blood biochemical test.

Ginseng is the root of the Araliaceae plant ginseng. More than 30 kinds of panaxoside and polysaccharide could be separated from the ginseng.

Largehead atractylodes rhizome is the dry rhizome of the Asteraceae plant Atractylodes macrocephala Koidz. The largehead atractylodes rhizome is bitter, sweet, warm, and benefit for spleen and stomach. The largehead atractylodes rhizome could strengthen the spleen, tonify vitality, eliminating dampness, promote dieresis, suppress sweating, and prevent abortion. The largehead atractylodes rhizome is indicated for asthenia of the spleen, deficiency of food, abdominal distention, diarrhea, phlegm retention, giddiness, palpitation, edema, apontaneous perspiration, and fetal irritability.

Indian bread is a fungus parasitizing on the root of pine trees. The Indian bread is sweet in taste, bland in flavour, and neutral in nature. The Indian bread is benefit for heart, lung, spleen, and kidney. The Indian bread has functions of promoting dieresis, excreting dampness, strengthening spleen and stomach, relieving mental stress.

Yamaimo is the root of yamaimo plant. The yamaimo is sweet in taste, warm, neutral in nature. The yamaimo is benefit for lung, spleen, and kidney. The yamaimo is indicated for weakness of the spleen and the stomach, listlessness, myasthenia, inappetence, prologed diarrhea and dysentery, deficiency of lung-vitality, dryness of the lung, phlegm dyspnea, cough, deficiency of kidney, soreness of the waist and knees, weakness of the lower extremity, diabetes, pollakiuria, emission and premature ejaculation, leukorrhagia, blennorrhea, red swollen skin, adiposis, etc.

Lotus seed is the dry mature seed of the lotus, which is a Nymphaeaceae aquatic herbaceous plant. The lotus seed is sweet in taste, cool in nature, and avirulent. The lotus seed is benefit for the spleen, the kidney, and the heart. The lotus seed has the functions of clearing away the heart-fire, activating the spleen-vitality, strengthening the spleen, anti-diarrhea, nourishing the heart, tranquilizing the mind, improving the eyesight, strengthening the vitality of the spleen and the stomach, cultivating the mentality, strengthening spleen and stomach, stopping emission, strengthening the kidney, treating spontaneous emission and leukorrhagia, and nourishing the archaeus. The lotus seed is indicated for hypochondriac discomfort, insomnia, weakness of the spleen, long-lasting diarrhea, sticky loose stools, protracted dysentery, lumbago, apontaneous emission of males, and leuhorrhagia with reddish discharge of females. The lotus seed could also prevent premature birth, abortion, and loins soreness of the pregnant woman.

Hawthorn fruit is the dry mature fruit of Shan Lihong or hawthorn, which is a Rosaceae Maloideae plant. The hawthorn fruit is sour and sweet in taste, slightly warm in nature. The hawthorn fruit is benefit for the spleen, stomach, and liver. The hawthorn fruit has functions of improving appetite, promoting digestion, relieving dyspepsia, promoting blood circulation, desslpating blood stasis, reducing phlegm, and promoting the circulation of vitality.

Germinated barley is the dried germinant mature fruit of the gramineae plant *Hordeum vulare L.* The germinated barley is sweet in taste, neutral in nature. The germinated barley is benefit for spleen and stomach. The germinated barley has functions of promoting the circulation of vitality and digestion, strengthening the spleen, improving appetite, suppression of lactation, and relieving flatulence. The germinated barley is indicated for dyspepsia, abdominal swelling and pain, weakness of the spleen, deficiency of food, galactostasis, distending pain in the breast, and delectation of woman.

*Rizoma alismatis* is the tuber of Alismataceae plant *Rizoma alismatis*. The *Rizoma alismatis* is sweet in taste, bland in flavor, cold in nature. The *Rizoma alismatis* is benefit for the kidney and bladder. The *Rizoma alismatis* has the functions of promoting dieresis, excreting dampness, letting off heat, and treating stranguria. The *Rizoma alismatis* is indicated for difficult urination, heat gonorrhea, painful and diffecult hematuria, edema, turgor, diarrhea, dizziness due to phlegm-retention, and apontaneous emission.

Tangerine peel is the peel of the Rutaceae plant tangerine. The tangerine peel is acrid and bitter in taste, and warm in nature. The tangerine peel is benefit for the spleen and the lung. The tangerine peel has functions of regulating the flow of vitality and the middle warmer, eliminating dampness, and reducing phlegm. The tangerine peel is indicated for stagnation of vitality in the spleen and stomach, distension in the abdomen, vomiting, or chest distress, anorexia, and soft stool due to stagnation of turbid dampness.

Liquorice root is the root and rhizome of the dicotyledon leguminosae liquorice. The liquorice root is neutral in nature, and sweet in taste. The liquorice root is benefit for twelve regular channels. The liquorice root has pharmacological actions of detoxication, inducing expectoratin, anodyne, relaxing the muscular spasm, even anticarcinogen. The liquorice root is indicated for weakness of the spleen and the stomach, lassitude, heart palpitation, short breath, cough, abundant expectoration, epigastric sag, spasm and pain of limbs, carbuncle, and sore. The liquorice root could alleviate the toxicity and the drastic actions of drug.

SUMMARY OF THE PRESENT INVENTION

An object of the present invention is to provide a pharmaceutical composition for strengthening spleen and stomach and a preparation method therefor.

The method provided by the present invention, comprises:

mixing following four substances to obtain a mixture, i.e., the pharmaceutical composition for strengthening spleen and stomach, wherein the four substances are (A) ginseng ethanol extract, (B) volatile oil of largehead atractylodes rhizome and tangerine peel, (C) aqueous extract of Indian bread, yamaimo, lotus seed, tangerine peel, liquorice root, hawthorn fruit, germinated barley, largehead atractylodes rhizome and rhizoma alismatis, and (D) fermentation broth of fruits and vegetables.

The substance (A) is prepared by a method comprising a step of extracting an extract from ginseng with ethanol water by a reflux extraction to obtain the ginseng ethanol extract.

The substance (B) is prepared by a method comprising steps of soaking largehead atractylodes rhizome and tangerine peel in water, distilling the largehead atractylodes rhizome and the tangerine peel to obtain distillate and dregs, and collecting the distillate to obtain the volatile oil of largehead atractylodes rhizome and tangerine peel.

The substance (C) is prepared by a method comprising steps of mixing Indian bread, yamaimo, lotus seed, liquorice root, hawthorn fruit, germinated barley, rhizoma alismatis, the dregs obtained in preparation of the substance (B), and water, processing decoction and filtering, collecting filtrate, adding absolute ethyl alcohol, statically standing, and collecting clear solution to obtain the aqueous extract of Indian bread, yamaimo, lotus seed, tangerine peel, liquorice root, hawthorn fruit, germinated barley, largehead atractylodes rhizome, and rhizoma alismatis.

The substance (D) is prepared by a method comprising steps of mixing fruits, vegetables, bacteria liquid of *Lactobacillus acidophilus*, bacteria liquid of *Bifidobactreium longum*, bacteria liquid of *Lactobacillus delbrueckii* subsp. *bulgaricus*, and bacteria liquid of *Streptococcus thermophilus*, processing fermentation to obtain a fermentation product, i.e., the fermentation broth of fruits and vegetables.

A mass ratio of the ginseng, the largehead atractylodes rhizome, the Indian bread, the liquorice root, the tangerine peel, the yamaimo, the lotus seed, the hawthorn fruit, the germinated barley, and the rhizoma alismatis is (1.5~2.5): (1.5~2.5):(1.5~2.5):(0.5~1.5):(0.5~1.5):(1.5~2.5):(1.5~2.5):(0.5~1.5):(0.5~1.5):(0.5~1.5).

The mass ratio of the ginseng, the largehead atractylodes rhizome, the Indian bread, the liquorice root, the tangerine peel, the yamaimo, the lotus seed, the hawthorn fruit, the germinated barley, and the rhizoma alismatis is preferably embodied as (1.5, 2 or 2.5):(1.5, 2 or 2.5):(1.5, 2 or 2.5):(0.5, 1 or 1.5):(0.5, 1 or 1.5):(1.5, 2 or 2.5):(1.5, 2 or 2.5):(0.5, 1 or 1.5):(0.5, 1 or 1.5):(0.5, 1 or 1.5).

In a preparation method of the substance (A), a period of the reflux extraction every time is 2 h~5 h, wherein the period of the reflux extraction is preferably embodied as 2 h, 3 h or 5 h.

A concentration of the ethanol water is 70% (volume percent).

In a preparation method of the substance (B), a soaking period is (1~60) min, wherein the soaking period is preferably embodied as 1 min, 30 min, or 60 min.

A distillating temperate is 90° C.~100° C., wherein the distillating temperature is preferably embodied as 90° C., 95° C., or 100° C.

In a preparation method of the substance (C), a decoction temperature is 90° C.~100° C., wherein the decoction temperature is preferably embodied as 90° C., 95° C., or 100° C. A decoction period is 1 h~2 h, wherein the decoction period is preferably embodied as 1 h, or 2 h.

The step of adding the absolute ethyl alcohol comprises adding the ethyl alcohol to the filtrate, until a volume percent of the ethyl alcohol in the filtrate is 70%.

In a preparation method of the substance (D), a fermentation temperature is 18° C.~37° C., wherein the fermentation temperature is preferably embodied as 18° C., 23° C., or 37° C. A fermentation period is 10 days~180 days, wherein the fermentation period is preferably embodied as 10 days, 15 days, or 180 days. A fermentation method comprises stirring while fermentation.

The preparation method of the substance (A) further comprises steps of:

removing ethanol from the extract, and processing concentration and drying to obtain a dried product, i.e., the ginseng ethanol extract.

The preparation method of substance (C) further comprises steps of removing ethyl alcohol from the clear solution after the step of collecting the clear solution, processing filtering to obtain filtrate, and concentrating and drying the filtrate to obtain a dried product, i.e., the aqueous extract of Indian bread, yamaimo, lotus seed, tangerine peel, liquorice root, hawthorn fruit, germinated barley, largehead atractylodes rhizome, and rhizoma alismatis.

The preparation method of the substance (D) further comprises steps of:

smashing the fruits and the vegetables into pieces of 40~50 meshes before the step of fermentation;

after the step of fermentation, filtering the fermentation product, collecting filtrate, processing ultrafiltration, and collecting liquid produced by the ultrafiltration, i.e., the fermentation broth of fruits and vegetables.

The step of ultrafiltration comprises ultrafiltering the filtrate in a molecular weight of 100,000, wherein a liquid inlet pressure is 1.3 kg, and a liquid outlet pressure is 0.5 kg.

The fruits and the vegetables refer to a mixture of following 54 kinds of fruits and vegetables, which are konjak, eggplant, asparagus, spinach, bean sprout, broccoli, cabbage, radish, cucumber, peas, red pepper, celery, scallion, garlic, grapes, grapefruit, watermelon, peach, tangerine, blue berry, sweet orange, banana, litchi, balsam pear, leek, pomegranate, pitaya, carrot, tomato, Chinese cabbage, parsley, bell pepper, lettuce, pear, ginger, taro, kidney bean, pumpkin, lotus root, cherry, kiwi fruit, plum, strawberry, fig, kumquat, mandarin orange, Nanguo pear, cantaloup, Hami melon, papaya, onion, mulberry, sugar beet, and lemon.

Mass of each fruit or vegetable is equal with each other.

In the preparation method of the substance (D), every 1 L of the mixture is prepared by a step of mixing (5~50) g of the ginseng ethanol extract, (5~50) g of the volatile oil of largehead atractylodes rhizome and tangerine peel, (5~200) g of the aqueous extract of Indian bread, yamaimo, lotus seed, tangerine peel, liquorice root, hawthorn fruit, germinated barley, largehead atractylodes rhizome and rhizoma alismatis, and the fermentation broth of fruits and vegetables, wherein a volume of the mixture is up to 1 L by adding the fermentation broth of fruits and vegetables.

Every 1 L of the mixture is preferably prepared by a step of mixing (5, 25, or 50) g of the ginseng ethanol extract, (5, 30, or 50) g of the volatile oil of largehead atractylodes rhizome and tangerine peel, (5, 150, 200) g of the aqueous extract of Indian bread, yamaimo, lotus seed, tangerine peel, liquorice root, hawthorn fruit, germinated barley, largehead atractylodes rhizome and rhizoma alismatis, and the fermentation broth of fruits and vegetables, wherein a volume of the mixture is up to 1 L by adding the fermentation broth of fruits and vegetables.

In the preparation method of the substance (A), a proportion of the ethanol water and the ginseng is (1~10) ml: 1 g, wherein the proportion of the ethanol water and the ginseng is preferably embodied as (1, 5, or 10) ml: 1 g.

In the preparation method of the substance (B), a proportion of the largehead atractylodes rhizome, the tangerine peel and the water is (1~10) g:(1~10) g:(5~50) ml, wherein the proportion of the largehead atractylodes rhizome, the tangerine peel and the water is preferably embodied as (1, 2, or 10) g:(1, 5, or 10) g:(5, 15, or 50) ml.

In the preparation method of the substance (C), a proportion of the Indian bread, the yamaimo, the lotus seed, the liquorice root, the hawthorn fruit, the germinated barley, the rhizoma alismatis, and water is (1~10) g:(1~10) g:(1~10) g:(1~10) g:(1~10) g:(1~10) g:(1~10) g:(5~100) ml, wherein the proportion of the Indian bread, the yamaimo, the lotus seed, the liquorice root, the hawthorn fruit, the germinated barley, the rhizoma alismatis, and water is preferably embodied as (1, 2, or 10) g:(1, 2, or 10) g:(1, 2, or 10) g:(1, 5, or 10) g:(1, 5, or 10) g:(1, 5, or 10) g:(1, 5, or 10) g:(50, 60, or 100) ml.

In the preparation method of the substance (D), a proportion of the bacteria liquid of *Lactobacillus acidophilus*, the bacteria liquid of *Bifidobactreium longum*, the bacteria liquid of *Lactobacillus delbrueckii* subsp. *bulgaricus*, the bacteria liquid of *Streptococcus thermophilus*, the fruits and vegetables, and water is (2000~8000) ml:(2000~8000) ml:(2000~8000) ml:(2000~8000) ml:(1000~1500) kg:(1000~1500) kg, wherein the proportion of the bacteria liquid of *Lactobacillus acidophilus*, the bacteria liquid of *Bifidobactreium longum*, the bacteria liquid of *Lactobacillus delbrueckii* subsp. *bulgaricus*, the bacteria liquid of *Streptococcus thermophilus*, the fruits and vegetables, and water is preferably embodied as (2000, 5000, or 8000) ml:(2000, 5000, or 8000) ml:(2000, 5000, or 8000) ml:(2000, 5000, or 8000) ml:(1000, 1200, or 1500) kg:(1000, 1200, or 1500) kg.

The bacteria liquid of *Lactobacillus acidophilus* is prepared by a method comprising: fermenting and cultivating Lactobacillus acidophilus to obtain a fermented product, i.e., the bacteria liquid of *Lactobacillus acidophilus*. A fermenting temperature is 20° C.~41° C., wherein the fermenting temperature is preferably embodied as 20° C., 37° C., or 41° C. A fermenting period is 15 h~36 h, wherein the fermenting period is preferably embodied as 15 h, 16 h, or 36 h.

The bacteria liquid of *Bifidobactreium longum* is prepared by a method comprising: fermenting and cultivating *Bifidobactreium longum* to obtain a fermented product, i.e., the bacteria liquid of *Bifidobactreium longum*. A fermenting temperature is 20° C.~41° C., wherein the fermenting temperature is preferably embodied as 20° C., 37° C., or 41° C. A fermenting period is 15 h~36 h, wherein the fermenting period is preferably embodied as 15 h, 16 h, or 36 h.

The bacteria liquid of *Lactobacillus delbrueckii* subsp. *bulgaricus* is prepared by a method comprising steps of: fermenting and cultivating *Lactobacillus delbrueckii* subsp. *bulgaricus* to obtain a fermented product, i.e., the bacteria liquid of *Lactobacillus delbrueckii* subsp. *bulgaricus*. A fermenting temperature is 20° C.~41° C., wherein the fermenting temperature is preferably embodied as 20° C., 37° C., or 41° C. A fermenting period is 15 h~36 h, wherein the fermenting period is preferably embodied as 15 h, 16 h, or 36 h.

The bacteria liquid of *Streptococcus thermophilus* is prepared by a method comprising steps of: fermenting and cultivating *Streptococcus thermophilus* to obtain a fermented product, i.e., the bacteria liquid of *Streptococcus thermophilus*. A fermenting temperature is 20° C.~41° C., wherein the fermenting temperature is preferably embodied as 20° C., 37° C., or 41° C. A fermenting period is 15 h~36 h, wherein the fermenting period is preferably embodied as 15 h, 16 h, or 36 h.

The *Lactobacillus acidophilus* is preferably embodied as Lactobacillus acidophilus CGMCC 1.1854, the *Bifidobactreium longum* is preferably embodied as *Bifidobactreium longum* CGMCC 1.2186, the *Lactobacillus delbrueckii* subsp. *bulgaricus* is preferably embodied as *Lactobacillus delbrueckii* subsp. *bulgaricus* CGMCC 1.1480, and the *Streptococcus thermophilus* is preferably embodied as *Streptococcus thermophilus* CGMCC 1.2471.

A medium of fermenting and cultivating is prepared by a method comprising: mixing 10 g of peptone, 10 g of beef extract, 5 g of yeast extract, 20 g of glucose, 1 g of tween-80, 2 g of $K_2HPO_4$, 1 g of tween-80, 5 g of NaAC, 2 g of ammonium citrate tribasic, 0.2 g of $MgSO_4$, 0.05 g of $MnSO_4$, and water, wherein a volume of the medium is up to 1 L by adding the water. A medicine for reducing fatigue prepared by the method described as above is also in a protecting range of the present invention.

The largehead atractylodes rhizome is preferably embodied as parched largehead atractylodes rhizome, the lotus seed is preferably embodied as parched lotus seed, the hawthorn fruit is preferably embodied as parched hawthorn fruit, and the germinated barley is preferably embodied as parched germinated barley.

A medicine for strengthening spleen and stomach prepared is in the protecting range of the present invention.

Experiments in the present invention proves that the ginseng extract, the volatile oil of largehead atractylodes rhizome and tangerine peel, the aqueous extract of Indian bread, yamaimo, lotus seed, tangerine peel, liquorice root, hawthorn fruit, germinated barley, largehead atractylodes rhizome and rhizoma alismatis, enzyme of the fruits and vegetables (fermentation broth) extracted in the present invention have short extracting periods. The medicine for strengthening spleen and stomach could be prepared with the above raw materials. People with low immunity in China are mostly in sub-health, and associated with symptoms of high blood sugar. To solve this problem, seasonings in the present invention is preferably embodied as Baisheng sugar, in such a manner that a dosage of sweeteners tending to raise the blood sugar, such as glucose and sucrose, is reduced to benefit more people.

These and other objectives, features, and advantages of the present invention will become apparent from the following detailed description, the accompanying drawings, and the appended claims.

DETAILED DESCRIPTION OF THE PREFERRED EMBODIMENT

Experimental methods used in following embodiments are all conventional method, if there is no special instruction.

Material, reagents, etc. used in the following embodiments could all be obtained by a commercial way, if there is no special instruction.

Example 1

Preparing Ginseng Enzyme Composition for Strengthening Spleen and Stomach

Method 1:

Raw materials of active constituent of the ginseng enzyme composition is listed as followed, which are 200 g of ginseng, 200 g of parched largehead atractylodes rhizome, 200 g of Indian bread, 100 g of liquorice root, 100 g of tangerine peel, 200 g of yamaimo, 200 g of parched lotus seed, 100 g of parched hawthorn fruit, 100 g of parched germinated barley, and 100 g of rhizoma alismatis.

I. Preparing Ginseng Extract Comprises:
1. preparing the raw materials, wherein the ginseng (JiLin Zixin pharmaceutical co., LTD.) complies with regulations of <Pharmacopoeia of the Chinese People's Republic of China>, and qualities of the ginseng is strictly monitored according to enterprise standard requirements, before being fed;
2. weighing out the ginseng according to formula, processing washing and draining, processing reflux extraction twice with ethanol water having a concentration of 70% and a dosage 10 times (v/w) the dosage of the ginseng, wherein extracting period of every time is 3 h, processing filtering, combining filtrate, reducing pressure, and recycling ethanol; and
3. concentrating the filtrate until relative density of the filtrate is 1.10~1.15 (60° C. 0.07 MPa), and processing spray drying (inlet temperature is 170° C., and outlet temperature is 70° C.) to obtain spray drying powder, i.e., the ginseng extract.

II. Preparing Volatile Oil of Largehead Atractylodes Rhizome and Tangerine Peel Comprises:
1. preparing the raw materials, wherein the largehead atractylodes rhizome and the tangerine peel (JiLin Zixin pharmaceutical co., LTD.) complies with regulations of <Pharmacopoeia of the Chinese People's Republic of China>, and qualities of the largehead atractylodes rhizome and the tangerine peel is strictly monitored according to enterprise standard requirements, before being fed; and
2. weighing out the largehead atractylodes rhizome and the tangerine peel according to the formula, processing washing and draining, soaking the largehead atractylodes rhizome and the tangerine peel in water for 30 min (proportion of the largehead atractylodes rhizome, the tangerine peel, and water is 2 g:1 g:15 ml), wherein dosage of the water added is preferably of which the water could just submerge medicinal materials, the dosage of the water is generally 5 times the dosage of the medicinal materials, and distilling temperature is 100° C., collecting the distillate with another container in a proportion of 5:1, (The volume collected is ⅕ the volume of the distillate, and the volatile oil is extracted completely at this time) and collecting remaining medicine in a distilling container to obtain largehead atractylodes rhizome slag and tangerine peel slag.

III. Preparing Aqueous Extract of Indian Bread, Yamaimo, Lotus Seed, Tangerine Peel, Liquorice Root, Hawthorn Fruit, Germinated Barley, Largehead Atractylodes Rhizome and Rhizoma Alismatis Comprises:
1. preparing the raw materials, wherein the Indian bread, the yamaimo, the lotus seed, the liquorice root, the hawthorn fruit, the germinated barley, and the rhizoma alismatis, (JiLin Zixin pharmaceutical co., LTD.) complies with regulations of <Pharmacopoeia of the Chinese People's Republic of China>, and qualities of the Indian bread, the yamaimo, the lotus seed, the liquorice root, the hawthorn fruit, the germinated barley, and the rhizoma alismatis, is strictly monitored according to enterprise standard requirements, before being fed;
2. weighing out the Indian bread, the yamaimo, the lotus seed, the liquorice root, the hawthorn fruit, the germinated barley, and the rhizoma alismatis according to the formula, and processing washing and draining; and
3. mixing the Indian bread, the yamaimo, the lotus seed, the liquorice root, the hawthorn fruit, the germinated barley, and the rhizoma alismatis with water, processing decoction twice, wherein decoction temperature is 100° C., dosages of the water are respectively 6 times and 5 times a dosage of medicinal material, periods are respectively 2 h and 1 h, combining filtrate of two times, concentrating the filtrate until relative density of the filtrate is 1.12~1.20 (80~90° C., reduced pressure concentration), adding ethanol until concentration of the ethanol is 70%, static standing for 24 h, collecting clear solution, recycling all of the ethanol, processing filtering, concentrating the filtrate until relative density of the filtrate is 1.10~1.15 (60° C., 0.07 MPa), and processing spray drying (inlet temperature is 170° C., and outlet temperature is 70° C.) to obtain spray drying powder, i.e., the aqueous extract, wherein in the first time of decoction, proportion of the Indian bread, the yamaimo, the lotus seed, the tangerine peel, the liquorice root, the hawthorn fruit, the germinated barley, the largehead atractylodes rhizome, the rhizoma alismatis, and water is 2 g:2 g:2 g:5 g:5 g:5 g:60 ml.

IV. Preparing Fermentation Broth of Fruits and Vegetables
1. The Fruits and Vegetables Selected

TABLE 1

Fruits and vegetables

| Material | Nutritional ingredient | Material | Nutritional ingredient |
| --- | --- | --- | --- |
| Konjac | Vitamin B1, B2, citric acid, fermentation product | Carrot | Vitamin A, carotene, fermentation product |
| Eggplant | Vitamin A, B1, B2, C, fermentation product | Tomato | Vitamin A, carotene, citric acid, fermentation product |
| Asparagus | Vitamin B1, B2, citric acid, fermentation product | Chinese cabbage | Vitamins, mineral substances, fermentation product |
| Spinach | Vitamin A, C, ferrum, calcium, fermentation product | Parsley | Vitamins, mineral substances, fibers, fermentation product |
| Bean sprout | Vitamin, saponin, amino acid, fermentation product | Bell pepper | Vitamin C, mineral substances, fermentation product |
| Broccoli | Vitamin B1, B2, citric acid, fermentation product | Lettuce | Vitamin A, mineral substances, fermentation product |
| Cabbage | Vitamin B1, B2, citric acid, fermentation product | Pear | Fructose, mineral substances, fermentation product |
| Radish | Vitamin B1, B2, citric acid, fermentation product | Ginger | Vitamins, mineral substances, fermentation product |
| Cucumber | Vitamin B1, B2, citric acid, fermentation product | Taro | Vitamin B1, B2, C, mineral substances, fermentation product |
| Pea | Vitamin B1, B2, citric acid, fermentation product | Kidney beans | Vitamin B1, B2, citric acid, fermentation product |

TABLE 1-continued

Fruits and vegetables

| Material | Nutritional ingredient | Material | Nutritional ingredient |
|---|---|---|---|
| Red pepper | Vitamin B1, B2, citric acid, fermentation product | Pumpkin | Carotene, mineral substances, fermentation product |
| Celery | Vitamin B1, B2, citric acid, fermentation product | Lotus root | Ferrum, tannin, fermentation product |
| Scallion | Vitamin B1, B2, citric acid, fermentation product | Cherry | mineral substances, fermentation product |
| Garlic | Vitamin B1, B2, citric acid, fermentation product | Kiwi fruit | Vitamin C, fermentation product |
| Grapes | Vitamin B1, B2, citric acid, fermentation product | Plum | organic acid, vitamins, fermentation product |
| Grapefruit | Vitamin B1, B2, citric acid, fermentation product | Strawberry | Vitamin C, mineral substances, ellagic acid, fermentation product |
| Watermelon | Vitamin B1, B2, citric acid, fermentation product | Fig | fermentation product, vitamins, mineral substances |
| Peach | Vitamin B1, B2, citric acid, fermentation product | Kumquat | Vitamin B1, B2, C, fermentation product |
| Tangerine | Vitamin B1, B2, C, fermentation product | Mandarin orange | Vitamin C, citric acid, fermentation product |
| Blueberry | Vitamin B1, B2, citric acid, fermentation product | Nanguo pear | Vitamin B1, B2, C, citric acid, fermentation product |
| Sweet orange | Vitamin B1, B2, citric acid, fermentation product | Cantaloup | Vitamin B1, B2, citric acid, fermentation product |
| Banana | Vitamin B1, B2, citric acid, fermentation product | Hami melon | Fructose, potassium, vitamin A, fermentation product |
| Litchi | Vitamin B1, B2, citric acid, fermentation product | Papaya | Vitamin B, C, E, citric acid, carotene, fermentation product |
| Balsam pear | Vitamin B1, B2, citric acid, fermentation product | Onion | Vitamin B, C, carotene, fermentation product |
| Leek | Vitamin B1, B2, citric acid, fermentation product | Mulberry | Vitamin B1, B2, citric acid, fermentation product |
| Pomegranate | Vitamin B1, B2, citric acid, fermentation product | Sugar beet | Betaine, fermentation product |
| Pitaya | Vitamin B1, B2, citric acid, fermentation product | Lemon | citric acid, fermentation product |

2. Fermenting the Fruits and the Vegetables

1) Selecting and Buying Strains

Probiotic strains are bought from micro-biology institute of Chinese Sciences Academy, the probiotics are Lactobacillus acidophilus CGMCC 1.1854, Bifidobactreium longum CGMCC 1.2186, Lactobacillus delbrueckii subsp. bulgaricus CGMCC 1.1480, and Streptococcus thermophilus CGMCC 1.2471. All of the strains are preserved in sand tube, and are used as original strains.

2) Preparing Master Seeds

Preparing the master seeds of the probiotics (Generations of transfer of the mater seeds is not more than 10, and the generations in the present invention is 4) comprises:

(1) taking 1/10 of the sand tube of Lactobacillus acidophilus CGMCC 1.1854, Bifidobactreium longum CGMCC 1.2186, Lactobacillus delbrueckii subsp. bulgaricus CGMCC 1.1480, and Streptococcus thermophilus CGMCC 1.2471 with a sterile stainless steel spoon, wherein rest of the probiotics is cryopreserved, respectively inoculating the probiotics in 50 ml of MRS liquid medium (250 triangular flask) (10 g/l peptone, 10 g/l beef extract, 5 g/l yeast extract, 20 g/l glucose, 1 g/l tween-80, 2 g/l $K_2HPO_4$, 1 g/l tween-80, 5 g/l NaAC, 2 g/l ammonium citrate tribasic, 0.2 g/l $MgSO_4$, 0.05 g/l $MnSO_4$, sterilization in a temperature of 121° C. for 20 min), and culturing the probiotics on a shaking table in a speed of 100 r/min and a temperature of 37° C. for 16 h;

(2) respectively taking one loop of each probiotics with a inoculating loop, respectively streak inoculating the probiotics in MRS solid medium (10 g/l peptone, 10 g/l beef extract, 5 g/l yeast extract, 20 g/l glucose, 1 g/l tween-80, 2 g/l $K_2HPO_4$, 1 g/l tween-80, 5 g/l NaAC, 2 g/l ammonium citrate tribasic, 0.2 g/l $MgSO_4$, 0.05 g/l $MnSO_4$, 1.5% agar, sterilization in a temperature of 121° C. for 20 min), culturing the probiotics in a incubator in a temperature of 37° C. for 16 h;

(3) respectively taking a bacterial colony which is most eugenic in each probiotics, respectively inoculating the bacterial colony in 50 ml of the MRS liquid medium, and culturing the bacterial colony on the shaking table in a speed of 180 r/min and a temperature of 30° C. for 16 h;

(4) respectively inoculating the bacterial colony in 500 ml of the MRS liquid medium, culturing the bacterial colony on the shaking table in a speed of 100 r/min and a temperature of 37° C. for 16 h, adding glycerol to a concentration of 20%, shaking up, storing the probiotics by 1 ml into freezing tubes, which are used as the master seeds of Lactobacillus acidophilus, Bifidobactreium longum, Bifidobacterium breve, and Streptococcus thermophilus, preserving in a temperature of −40° C.

3. Preparing Working Seeds

Preparing working seeds of the probiotics comprises steps of: (The transfer generations of working seeds is not more than 5, and the transfer generations in the present invention is 4.)

(1) respectively taking the master seeds of Lactobacillus acidophilus CGMCC 1.1854, Bifidobactreium longum CGMCC 1.2186, Lactobacillus delbrueckii subsp. bulgaricus CGMCC 1.1480, and Streptococcus thermophilus CGMCC 1.2471 with the sterile inoculating loop, respectively streak inoculating the master seeds on the MRS solid medium, and culturing the master seeds in the incubator in a temperature of 37° C. for 16 h;

(2) respectively taking a bacterial colony which is most eugenic in each probiotics, respectively inoculating the bacterial colony in 50 ml of the MRS liquid medium, and culturing the bacterial colony on the shaking table in a speed of 100 r/min and a temperature of 37° C. for 16 h;

(3) respectively inoculating the bacterial colony in 500 ml of the MRS liquid medium, and culturing the bacterial colony on the shaking table in a speed of 100 r/min and a temperature of 37° C. for 16 h; and (4) respectively inoculating the bacterial colony in 5000 ml of the MRS liquid medium, and culturing the bacterial colony on the shaking table in a speed of 100 r/min and a temperature of 37° C. for 16 h to obtain bacteria liquid of *Lactobacillus acidophilus* CGMCC 1.1854, bacteria liquid of *Bifidobactreium longum* CGMCC 1.2186, bacteria liquid of *Lactobacillus delbrueckii* subsp. *bulgaricus* CGMCC 1.1480, and bacteria liquid of *Streptococcus thermophilus* CGMCC 1.2471, wherein above bacteria liquids are all whole fermenting products in the fermenting container.

4. Treating the Fruits and the Vegetables, Comprises Steps of:

1) Weighing the above materials;

2) washing the above materials, removing foreign substances, drying, and weighing; and 3) smashing the materials into pieces of 40~50 meshes, adding the materials into a fermenter; wherein practical feeding amount is 2400 kg for a fermenter of 3 t (Weight of effective solvents=3 t*0.8=2.4 t), and a proportion of the fruits and vegetables and water is 1:1, e.g. the weight of the fruits and vegetables is 1200 kg, and the weight of the water is 1200 kg.

5. Fermenting the Fruits and the Vegetables with Rapid Zymolyte, Comprises Steps of:

Adding 5000 ml of each of the bacteria liquid of *Lactobacillus acidophilus* CGMCC 1.1854, the bacteria liquid of *Bifidobactreium longum* CGMCC 1.2186, the bacteria liquid of *Lactobacillus delbrueckii* subsp. *bulgaricus* CGMCC 1.1480, and the bacteria liquid of *Streptococcus thermophilus* CGMCC 1.2471 into the fermenter, controlling the fermenting temperature being 23° C., stirring for 15 d;

3) filtering the fermenting product with a filter cloth of 200 meshes, and removing residues of the fruits and vegetables to obtain filtrate;

4) ultrafiltering the filtrate in a molecular weight of 100,000 (a liquid inlet pressure is 1.3 kg, and a liquid outlet pressure is 0.5 kg) to obtain 1200~1500 kg of clear liquid, sealing the clear liquid, preserving the clear liquid in a temperature of 4° C. to obtain the fermentation broth of fruits and vegetables.

6. Detecting

The fermentation broth of fruits and vegetables mainly comprises: lactic acid and acetic acid, so acidity is identified as characteristic components of the fermentation broth of fruits and vegetables, which is preferably embodied as followed.

The acidity of the fermentation broth of fruits and vegetables refers to ml number/volume of NaOH solution of 0.1N consumed to titrate 100 ml of the fermentation broth of fruits and vegetables, and 10 ml of sample of the fermentation broth of fruits and vegetables is usually used when detecting.

Detecting comprises steps of: taking 10 ml of the fermentation broth of fruits and vegetables, 20 ml of water, and 0.5 ml of phenolphthalein indicator, processing titration with NaOH standard solution of 0.1N until mixture turns to reddish without fading in a period of 30 seconds. Calculating formula: Acidity=volume of the NaOH standard solution of 0.1N consumed*10.

Result: The acidity of the product is 42.

V. Preparing the Composition

The exacts and the fermentation broth of fruits and vegetables are mixed according formula as followed. 25 g of the ginseng ethanol extract, 30 g of the volatile oil of largehead atractylodes rhizome and tangerine peel, 150 g of the aqueous extract of Indian bread, yamaimo, lotus seed, tangerine peel, liquorice root, hawthorn fruit, germinated barley, largehead atractylodes rhizome and rhizoma alismatis, and the fermentation broth of fruits and vegetables are mixed to obtain the composition, wherein the fermentation broth of fruits and vegetables supplements volume of the mixture to 10,000 ml, and the 10,000 ml of the mixture could be divided into 1000 bottles, 10 ml per bottle.

Method 2:

Raw materials of active constituent of the ginseng enzyme composition is listed as followed, which are 150 g of ginseng, 150 g of parched largehead atractylodes rhizome, 150 g of Indian bread, 50 g of liquorice root, 50 g of tangerine peel, 150 g of yamaimo, 150 g of parched lotus seed, 50 g of parched hawthom fruit, 50 g of parched germinated barley, and 50 g of rhizoma alismatis.

I. Preparing Ginseng Extract Comprises Steps of:

Extracting method is mainly same as method 1, except that the ginseng refluxing extracted with ethanol water having a concentration of 70% and a dosage 1 times (v/w) the dosage of the ginseng, wherein extracting period of every time is 2 h.

II. Preparing Volatile Oil of Largehead Atractylodes Rhizome and Tangerine Peel

Extracting method is mainly same as method 1, except that the proportion of the largehead atractylodes rhizome, the tangerine peel, and water is 1 g:5 g:5 ml, soaking period is 1 min, and the distilling temperature is 90° C.

III. Preparing Aqueous Extract of Indian Bread, Yamaimo, Lotus Seed, Tangerine Peel, Liquorice Root, Hawthorn Fruit, Germinated Barley, Largehead Atractylodes Rhizome and Rhizoma Alismatis Extracting method is mainly same as method 1, except that the proportion of the Indian bread, the yamaimo, the lotus seed, the tangerine peel, the liquorice root, the hawthorn fruit, the germinated barley, the largehead atractylodes rhizome, the rhizoma alismatis, and water is 1 g:1 g:1 g:1 g:1 g:1 g:50 ml, and the decoction temperature is 90° C.

IV. Preparing Fermentation Broth of Fruits and Vegetables

Extracting method is mainly same as method 1, except that 2000 ml of each of the bacteria liquid of *Lactobacillus acidophilus* CGMCC 1.1854, the bacteria liquid of *Bifidobactreium longum* CGMCC 1.2186, the bacteria liquid of *Lactobacillus delbrueckii* subsp. *bulgaricus* CGMCC 1.1480, and the bacteria liquid of *Streptococcus thermophilus* CGMCC 1.2471 are added, the weight of the fruits and vegetables added is 1000 kg, and the weight of the water is 1000 kg.

Fermenting temperature of the fermentation broth of fruits and vegetables is 18° C., and fermenting period is 10 d.

In the preparation of the bacteria liquid of *Lactobacillus acidophilus*, the bacteria liquid of *Bifidobactreium longum*, the bacteria liquid of *Lactobacillus delbrueckii* subsp. *bulgaricus*, and the bacteria liquid of *Streptococcus thermophilus*, fermenting temperatures are all 20° C., and fermenting periods are all 15 h.

Detecting method is same as method 1, and there is no marked difference in the result and the steps.

V. Preparing the Composition

The preparing method is mainly same as method 1, except that 5 g of the ginseng ethanol extract, 5 g of the volatile oil of largehead atractylodes rhizome and tangerine peel, 5 g of the aqueous extract of Indian bread, yamaimo, lotus seed, tangerine peel, liquorice root, hawthorn fruit, germinated barley, largehead atractylodes rhizome and rhizoma alismatis, and the fermentation broth of fruits and vegetables are mixed to obtain the composition, wherein the fermentation broth of fruits and vegetables supplements volume of the mixture to 10,000 ml.

Method 3:

Raw materials of active constituent of the ginseng enzyme composition is listed as followed, which are 250 g of ginseng, 250 g of parched largehead atractylodes rhizome, 250 g of Indian bread, 150 g of liquorice root, 150 g of tangerine peel, 250 g of yamaimo, 250 g of parched lotus seed, 150 g of parched hawthom fruit, 150 g of parched germinated barley, and 150 g of rhizoma alismatis.

I. Preparing Ginseng Extract Comprises Steps of:

Extracting method is mainly same as method 1, except that the ginseng refluxing extracted with ethanol water having a concentration of 70% and a dosage 5 times (v/w) the dosage of the ginseng, wherein extracting period of every time is 5 h.

II. Preparing Volatile Oil of Largehead Atractylodes Rhizome and Tangerine Peel

Extracting method is mainly same as method 1, except that the proportion of the largehead atractylodes rhizome, the tangerine peel, and water is 10 g:10 g:50 ml, soaking period is 60 min, and the distilling temperature is 95° C.

III. Preparing Aqueous Extract of Indian Bread, Yamaimo, Lotus Seed, Tangerine Peel, Liquorice Root, Hawthorn Fruit, Germinated Barley, Largehead Atractylodes Rhizome and Rhizoma Alismatis Extracting method is mainly same as method 1, except that the proportion of the Indian bread, the yamaimo, the lotus seed, the tangerine peel, the liquorice root, the hawthorn fruit, the germinated barley, the largehead atractylodes rhizome, the rhizoma alismatis, and water is 10 g:10 g:10 g:10 g:10 g:10 g:10 g:100 ml, and the decoction temperature is 95° C.

IV. Preparing Fermentation Broth of Fruits and Vegetables

Extracting method is mainly same as method 1, except that 8000 ml of each of the bacteria liquid of *Lactobacillus acidophilus* CGMCC 1.1854, the bacteria liquid of *Bifidobactreium longum* CGMCC 1.2186, the bacteria liquid of *Lactobacillus delbrueckii* subsp. *bulgaricus* CGMCC 1.1480, and the bacteria liquid of *Streptococcus thermophilus* CGMCC 1.2471 are added, the weight of the fruits and vegetables is 1500 kg, and the weight of the water is 1500 kg.

Fermenting temperature of the fermentation broth of fruits and vegetables is 37, and fermenting period is 180 d.

In the preparation of the bacteria liquid of *Lactobacillus acidophilus*, the bacteria liquid of *Bifidobactreium longum*, the bacteria liquid of *Lactobacillus delbrueckii* subsp. *bulgaricus*, and the bacteria liquid of *Streptococcus thermophilus*, fermenting temperature are all 41° C., and fermenting period is 36 h.

Detecting method is same as method 1, and there is no marked difference in the result and the steps.

V. Preparing the Composition

The preparing method is mainly same as method 1, except that 50 g of the ginseng ethanol extract, 50 g of the volatile oil of largehead atractylodes rhizome and tangerine peel, 200 g of the aqueous extract of Indian bread, yamaimo, lotus seed, tangerine peel, liquorice root, hawthorn fruit, germinated barley, largehead atractylodes rhizome and rhizoma alismatis, and the fermentation broth of fruits and vegetables are mixed to obtain the composition, wherein the fermentation broth of fruits and vegetables supplements volume of the mixture to 10,000 ml.

Example 2

Preparation of Oral Solution of Ginseng, Largehead Atractylodes Rhizome, and Indian Bread A conventional oral solution producing process is used to producing this product, and the producing process comprises steps of: mixing, filtering, instantaneous sterilization, bottling, capping, leakage detecting, checking transparent degree, outer packing, inspection, and entering warehouse, wherein the steps before leakage detecting are all processed in 100,000 class clean area. Producing process design and equipment conditions both conform to GMP requirement of China.

Specific producing method comprises steps of mixing the composition obtained in example 1 and seasoning (The seasoning is white granulated sugar, bought from Eurasia department of Changchun.), adding mixture into a liquid tank, stirring for 30 min to ensure uniformity, and instantaneous high temperature sterilization to obtain oral solution of ginseng, largehead atractylodes rhizome, and Indian bread.

2. Bottling the product into oral solution bottles comprises step of: bottling the product into oral solution bottles with an oral solution bottling machine, wherein every bottle is 10 ml, packing volume difference of product should be monitored while bottling to ensure that the difference is controlled in a difference range.

3. Capping comprises steps of: capping the oral solution with an oral solution capping machine, and screening non-conforming products.

4. Leakage detecting comprises a step of: detecting leakage of the oral solution capped with vacuum leakage detector.

5. Inner packing comprises a step of: packing with cardboard boxes, wherein every cardboard box comprises 10 bottles.

6. Outer packing comprises a step of: packing with corrugated cases.

7. Detecting comprises a step of detecting according to a enterprise standard.

8. Entering warehouse comprises a step of displacing the product into a warehouse after the product is inspected to be qualified.

Example 3

Experimental Research on how the Oral Solution of Ginseng, Largehead Atractylodes Rhizome, and Indian Bread Improves Digestion 1. Materials
1.1. Experimental Animals 60 mice of clean level and Kunming species weighing 18~22 g and 20 male rats of clean level and Wistar weighing 180~200 g are provided by animal experimental center of Jilin university.

1.2. Experimental Medicine
1.2.1. Medicine

The oral solution of ginseng, largehead atractylodes rhizome, and Indian bread is prepared in example 2, and Motilium tablets is produced by Xian-Janssen Pharmaceutical Ltd and has a specification of 100mg*30 pieces.

1.2.2. Preparing of Medicine

Motilium: 10mg of Motilium is added into 100ml of distilled water to obtain Motilium solution, wherein each milliliter of the Motilium solution contains 0.1mg of Motilium.

1.3. Main Agentia

Paraformaldehyde (E. Merk); Acetylthiocholine iodide (Fluka); Dextran blue 2000 (pharmacia); Sodium acetate (Shanghai chemical reagent station); Citron acid sodium (Qingdao marine chemical plant); Copper sulfate (Shenyang Hongvitality chemical plant); Potassium ferricyanide (Taizhou biochemical materials plant); and Four isopropyl phosphorous amides (Qingdao Marine chemical plant).

1.4. Main Apparatus

Cryostat frozen section machine; Desktop balance recorder; Full wavelength spectrophotometer, centrifugal sink lake; Optical microscope; Multimedia color pathological image analysis system, and OlympusPM-30 photographic system.

2. Method

All of counting data and measurement data are expressed as mean±standard deviation (x±s). Compare between two groups is tested by U/t, and analysis of variance (ANOVA) is used to compare multiple groups. The data are processed by medicine SAS statistical software package on the computer.

2.1. Detecting Advancing Function of Small Intestine of a Mouse 30 mice of Kunming species are taken, which have fasted for 20~24h. The mice are randomly divided into 3 groups, i.e., a control group, a group of oral solution of ginseng, largehead atractylodes rhizome, and Indian bread, and a Motilium group. Each group comprises 10 animals, tagged with picric acid. The group of oral solution of ginseng, largehead atractylodes rhizome and Indian bread are processed with intragastric administration by feeding stoste of the oral solution of ginseng, largehead atractylodes rhizome and Indian bread (20.0ml/kg). The Motilium group is processed with intragastric administration by feeding the Motilium solution (3.9mg/kg). The control group is processed with intragastric administration by feeding equivalent amount of physiological saline. After 90 minutes, each group is given 0.3ml of ink for intragastric administration. After 20 minutes, the mice are executed by cervical dislocation. For each mouse, an abdominal cavity is opened, a mesentery is separated, a length of intestinal canal is cut off from pylorus in an upper portion to ileocecus in a lower portion, and the length of intestinal canal is displaced on a tray. A small intestine is gently pulled into a straight line, and the length of the intestinal canal is measured as a total length of the small intestine. A distance between the pylorus and a front edge is defined as "advancing distance of the ink in the small intestine". An advancing rate of the ink is calculated by a formula.

Advancing rate of the ink(%)=advancing distance of the ink in the small intestine (cm)/the total length of the small intestine (cm)*100%

Comparing results of the advancing function of small intestine of the three groups is illustrated in Table 2.

TABLE 2

Comparison of advancing function of small intestine of the three groups (x ± s)

| Experimental group | Amount of animals | Total length of small intestine (cm) | Advancing distance of ink in small intestine (cm) | Advancing rate(%) |
|---|---|---|---|---|
| Control group | 10 | 41.02 ± 2.7959 | 26.450 ± 4.0445 | 64.27 ± 7.0015 |
| Ginseng largehead atractylodes rhizome and Indian bread oral solution group | 10 | 37.82 ± 3.3133 | 31.38 ± 4.2923Δ* | 83.017 ± 8.7961 |
| Motilium group | 10 | 37.82 ± 5.2087 | 27.0 ± 2.7406 | 71.938 ± 6.8437 |

Compared with the control group, $\Delta P < 0.01$.

Compared with the Motilium group, $*P < 0.05$.

Compared with the control group, $\Delta P<0.01$. Compared with the Motilium group, $*P<0.05$.

2.2. Detecting Gastric Emptying Function of a Mouse 30 mice are divided into a group of oral solution of ginseng, largehead atractylodes rhizome, and Indian bread, Motilium group, and a control group. Each group comprises 10 mice. The group of oral solution of ginseng largehead atractylodes rhizome and Indian bread is processed with intragastric administration by feeding the oral solution of ginseng largehead atractylodes rhizome and Indian bread of 20.0ml/kg. The Motilium group is processed with intragastric administration by feeding the Motilium solution of 3.9mg/kg. The control group is processed with intragastric administration by feeding equivalent volume of deionized water. After 10 minutes, 0.4ml of the dextran blue 2000 solution of 2% is given to each mouse. After 30 minutes, the mice are executed by cervical dislocation. For each mouse, all of stomach and intestines are taken out after opening abdominal cavity, and the stomach is cut off at a position of pylorus sphincter. Residual pigment (dextran blue 2000) in the stomach is fully dissolved in 2ml of deionized water, and solution containing pigment is centrifugally separated in 3500rpm for 15 minutes. Then supernatant is taken and filtered by glass cotton filter. Absorbance of filtrate is measured by giving a light of 620nm with a 723 type spectrophotometer, to obtain a stomach pigment residual quantity and calculate mean value of each group. The mean value of the control group is defined as 100%, and percentage of the mean values of other groups and the mean value of the control group is defined as relative stomach pigment residual rate.

TABLE 3

Comparison of stomach pigment residual rate of three groups (x ± s)

| Experimental group | Amount of animals | Somach pigment residual quantity | Rlative stomach pigment residual rate (%) |
|---|---|---|---|
| Control group | 10 | 186.6 ± 42.6 | 100 |
| Ginseng largehead atractylodes | 10 | 94.7 ± 23.6Δ* | 50.9Δ* |

TABLE 3-continued

Comparison of stomach pigment residual rate of three groups (x ± s)

| Experimental group | Amount of animals | Somach pigment residual quantity | Rlative stomach pigment residual rate (%) |
|---|---|---|---|
| rhizome and Indian bread oral solution group | | | |
| Motilium group | 10 | 152.3 ± 14.01 | 81.8 |

Compared with the control group, ΔP < 0.01.
Compared with the Motilium group, *P < 0.01.

2.3. Establishment of Animal Model

A characteristics of the rats is used according to a method of enraging stimulation. The characteristics of the rats is that the rats are grumpy and easy to be enraged, so anintense fighting between the rats could be caused by a low intensity stimulation. 20 male rats of clean level and Wistar provided by animal experimental center of Jilin university are randomly divided into 4 groups, i.e., three first model group and a control group. For the first model groups, tails of the rats are stimulated by being clipped with a forceps hamostatic, which is wrapped by a gauze in a top end, in such a manner that the rats are enraged, and fight with each other. Stimulation is processed for 30 minutes every time, every 3 hours once, and 4 times a day. After a week, intake of food and drink significantly decreases, and some rats even don't eat and drink at all. The rats are mainly tired. The hair of the rats becomes pale, withered, and yellow. Consequently, weights of the rats decrease. The rats in the first model groups present typical symptoms of disharmony between liver and stomach, and non-ulcer dyspepsia (NUD).

2.4. Detecting Gastric Motility Frequency and Amplitude of Rats

The rats in the first model groups, which present symptoms of disharmony between liver and stomach, are randomly divided into a second model group, a group of oral solution of ginseng, largehead atractylodes rhizome, and Indian bread, and a group of Motilium group. Each group comprises 5 rats. The group of oral solution of ginseng, largehead atractylodes rhizome, and Indian bread are treated with intragastric administration by feeding the oral solution of ginseng, largehead atractylodes rhizome, and Indian bread of 20.0ml/kg·d at twice. The Motilium group is treated with intragastric administration by feeding the Motilium solution of 2.7mg/kg.d at three times. The second model group is processed with intragastric administration by feeding equivalent amount of physiological saline. Each of the groups has a courses of 2 weeks. After the treatment is finished, the animal is anesthetized with urethane of 10%, and then fixed on a operating table in a supine position. An abdominal cavity of the rat is cut from a middle of an abdominal wall. A longitudinal muscle is found near a gastric antrumin in a greater gastric curvature. A near end of the longitudinal muscle is sutured by 1 needle to being fixed. A far end of the longitudinal muscle is sutured by 1 needle. A first end of a string is connected with the far end, and a second end of the string is connected with a tonotransducer. Motility frequencies and motility amplitudes of stomach begin to be recorded by a desktop balance recorder 1h after operations. An initial tension is set to 5mv. None of the experimental animals presents organic diseases such as ulcer, which is also observed from the experiments.

TABLE 4

Comparison of contraction amplitude of four groups of rats (x ± s)

| Experimental group | Amount of animals | Contraction amplitude |
|---|---|---|
| Control group | 5 | 18.72 ± 0.8818 |
| Second model group | 5 | 14.976 ± 0.9465 |
| Group of oral solution of ginseng, largehead atractylodes rhizome, and Indian bread | 5 | 21.024 ± 1.7972*▲ |
| Motilium group | 5 | 17.372 ± 1.6270* |

Compared with the control group, ΔP < 0.01.
Compared with second model group, *P < 0.01.
Compared with the Motilium group, ▲P < 0.05.

TABLE 5

Comparison of contraction frequency of four groups of rats (x ± s)

| Experimental group | Amount of animals | Contraction frequency (times/minutes) |
|---|---|---|
| Control group | 5 | 3.92 ± 0.1095 |
| Second model group | 5 | 2.526 ± 0.4604Δ |
| Group of oral solution of ginseng, largehead atractylodes rhizome, and Indian bread | 5 | 4.364 ± 0.4336* |
| Motilium group | 5 | 3.82 ± 0.2864 |

Compared with the control group, ΔP < 0.01.
Compared with second model group, *P < 0.01.
Compared with the Motilium group, ▲P < 0.05.

It is shown by experimental results that the rats in the second model group don't present organic diseases, such as ulcer, but the mechanical contraction frequency and the mechanical contraction amplitude of the stomach and the intestines of the second model group are significantly poorer than those of the control group, which proves that negative emotions, such as tension, anxiety, irritability, are important factors causing the non-ulcer dyspepsia.

It is improved by research that the oral solution of ginseng, largehead atractylodes rhizome, and Indian bread could recover normal mechanical motion of the stomach efficiently. After the model animals is treated by the present composition, the contraction frequency and the contraction amplitude of the stomach both increase significantly. The composition could also significantly improve the gastric emptying function and the advancing function of small intestine. In summary, the oral solution of ginseng, largehead atractylodes rhizome, and Indian bread could treat the non-ulcer dyspepsia efficiently.

The compositions prepared by the method 2 and the method 3 of the example 1 are detected by a method same as above, and results are also same as the composition 1 prepared by the method 1.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for preparing a pharmaceutical composition for strengthening spleen and stomach, comprising steps of:
preparing a substance (A), wherein the substance (A) is ginseng ethanol extracts, prepared by the steps of extracting extracts from ginseng with ethanol water by a reflux extraction, removing ethanol from the extracts, concentrating and drying to obtain the ginseng ethanol extracts;
preparing a substance (B), wherein the substance (B) is volatile oils of largehead atractylodes rhizome and tangerine peel, prepared by the steps of soaking largehead atractylodes rhizome and tangerine peel in water, distilling the largehead atractylodes rhizome and the tangerine peel to obtain distillate and dregs, and collecting the distillate to obtain the volatile oils of largehead atractylodes rhizome and tangerine peel;
preparing a substance (C), wherein the substance (C) is extracts of Indian bread, yamaimo, lotus seed, tangerine peel, liquorice root, hawthorn fruit, germinated barley, largehead atractylodes rhizome and rhizoma alismatis, prepared by the steps of mixing Indian bread, yamaimo, lotus seed, liquorice root, hawthorn fruit, germinated barley, rhizoma alismatis, the dregs obtained in preparation of the substance (B), and water, making a decoction and filtering, collecting filtrate, adding absolute ethyl alcohol, letting it stand in order to decant, collecting the clear solution, removing ethyl alcohol from the clear solution after the step of collecting the clear solution, filtering the solution to obtain a filtrate and concentrating and drying the filtrate to obtain the aqueous solution extracts of Indian bread, yamaimo, lotus seed, tangerine peel, liquorice root, hawthorn fruit, germinated barley, largehead atractylodes rhizome and rhizoma alismatis;
preparing a substance (D), wherein the substance (D) is fermentation broth of fruits and vegetables, prepared by the steps in order of mixing fruits, vegetables, bacteria liquid of *Lactobacillus acidophilus*, bacteria liquid of *Bifidobacterium longum*, bacteria liquid of *Lactobacillus delbrueckii* subsp. *bulgaricus*, and bacteria liquid of *Streptococcus thermophilus*, smashing the fruits and the vegetables into pieces with a size of 40-50 meshes, fermenting the mixture filtering the fermentation product, collecting the filtrate, ultrafiltering, and collecting the fermentation broth of fruits and vegetables produced by the ultrafiltration; and
mixing the substances (A), (B), (C) and (D) to obtain the pharmaceutical composition for strengthening spleen and stomach.

2. A method for preparing a pharmaceutical composition for strengthening spleen and stomach, comprising steps of:
preparing a substance (A), wherein the substance (A) is ginseng ethanol extracts, prepared by the a step of extracting extracts from ginseng with ethanol water by a reflux extraction to obtain the ginseng ethanol extracts;
preparing a substance (B), wherein the substance (B) is volatile oils of largehead atractylodes rhizome and tangerine peel, prepared by the steps of soaking largehead atractylodes rhizome and tangerine peel in water, distilling the largehead atractylodes rhizome and the tangerine peel to obtain distillate and dregs, and collecting the distillate to obtain the volatile oils of largehead atractylodes rhizome and tangerine peel;
preparing a substance (C), wherein the substance (C) is extracts of Indian bread, yamaimo, lotus seed, tangerine peel, liquorice root, hawthorn fruit, germinated barley, largehead atractylodes rhizome and rhizoma alismatis, prepared by the steps of mixing Indian bread, yamaimo, lotus seed, liquorice root, hawthorn fruit, germinated barley, rhizoma alismatis, the dregs obtained in preparation of the substance (B), and water, making a decoction and filtering, collecting filtrate, adding absolute ethyl alcohol, letting it stand in order to decant, and collecting the clear solution to obtain the aqueous solution extracts of Indian bread, yamaimo, lotus seed, tangerine peel, liquorice root, hawthorn fruit, germinated barley, largehead atractylodes rhizome and rhizoma alismatis;
preparing a substance (D), wherein the substance (D) is fermentation broth of fruits and vegetables, prepared by the steps in order of mixing fruits, vegetables, bacteria liquid of *Lactobacillus acidophilus*, bacteria liquid of *Bifidobacterium longum*, bacteria liquid of *Lactobacillus delbrueckii* subsp. *bulgaricus*, and bacteria liquid of *Streptococcus thermophilus*, and fermenting the mixture to obtain the fermentation broth of fruits and vegetables; and
mixing the substances (A), (B), (C) and (D) to obtain the pharmaceutical composition for strengthening spleen and stomach,
wherein the fruits and vegetables under (D) are a mixture of the following 54 kinds of fruits and vegetables:
konjak, eggplant, asparagus, spinach, bean sprout, broccoli, cabbage, radish, cucumber, peas, red pepper, celery, scallion, garlic, grapes, grapefruit, watermelon, peach, tangerine, blueberry, sweet orange, banana, litchi nut, balsam pear, leek, pomegranate, pitaya, carrot, tomato, Chinese cabbage, parsley, bell pepper, lettuce, pear, ginger, taro, kidney bean, pumpkin, lotus root, cherry, kiwi fruit, plum, strawberry, fig, kumquat, mandarin orange, Nanguo pear, cantaloupe, Hami melon, papaya, onion, mulberry, sugar beet, and lemon, wherein the
mass of each fruit or vegetable is equal with each other.

* * * * *